US012806303B2

(12) United States Patent
Kim et al.

(10) Patent No.: US 12,806,303 B2
(45) Date of Patent: Nov. 24, 2026

(54) AIR CLEANING AND DISINFECTION ROBOT AND OPERATING METHOD THE SAME

(71) Applicant: HDHyundai Robotics Co., Ltd., Daegu (KR)

(72) Inventors: Tae Hyun Kim, Daegu (KR); Jong Wook Kim, Daegu (KR); Jong Kyu Oh, Daegu (KR); Woo Jae Lee, Daegu (KR)

(73) Assignee: HDHYUNDAI ROBOTICS CO., LTD., Daegu (KR)

( * ) Notice: Subject to any disclaimer, the term of this patent is extended or adjusted under 35 U.S.C. 154(b) by 438 days.

(21) Appl. No.: 18/374,949

(22) Filed: Sep. 29, 2023

(65) Prior Publication Data

US 2024/0108778 A1 Apr. 4, 2024

(30) Foreign Application Priority Data

Sep. 30, 2022 (KR) ........................ 10-2022-0125825

(51) Int. Cl.

| | |
|---|---|
| ***A61L 9/14*** | (2006.01) |
| ***B25J 5/00*** | (2006.01) |
| ***B25J 11/00*** | (2006.01) |
| ***G05D 1/00*** | (2006.01) |

(52) U.S. Cl.

CPC ................. *A61L 9/14* (2013.01); *B25J 5/007* (2013.01); *B25J 11/0085* (2013.01); *G05D 1/0231* (2013.01); *A61L 2209/11* (2013.01); *A61L 2209/16* (2013.01)

(58) Field of Classification Search

CPC .................................... A61L 9/14; F24F 8/15

See application file for complete search history.

(56) References Cited

U.S. PATENT DOCUMENTS

2007/0050937 A1* 3/2007 Song ..................... A47L 9/0009 15/319
2016/0059424 A1 3/2016 Zachary et al.
2022/0142422 A1* 5/2022 Giarritta ............. A47L 11/4025

FOREIGN PATENT DOCUMENTS

JP 2018-513817 A 5/2018
KR 10-2007-0078846 A 8/2007

OTHER PUBLICATIONS

Office action from South Korean Patent Application No. 10-2022-0125825 dated Aug. 28, 2024.

* cited by examiner

*Primary Examiner* — Kevin Joyner
(74) *Attorney, Agent, or Firm* — Ladas & Parry, LLP

(57) ABSTRACT

Disclosed herein are an air cleaning and disinfection robot and a method of operating the same. The air cleaning and disinfection robot includes a driving unit configured to move autonomously in a target space, a plurality of air conditioning modules configured to manage air quality in the target space and detachably provided on the driving unit, a station on which the plurality of air conditioning modules are mounted, a docking unit configured to couple and separate the driving unit and each of the air conditioning modules to and from each other, and a detection unit configured to detect an operation environment of the target space, wherein the driving unit, based on information obtained by the detection unit, may selectively couple to and move with any one of the plurality of air conditioning modules.

18 Claims, 17 Drawing Sheets

AIR CLEANING AND DISINFECTION ROBOT AND OPERATING METHOD THE SAME

CROSS-REFERENCE TO RELATED APPLICATION

This application claims the benefit of Korean Patent Application No. 10-2022-0125825, filed on Sep. 30, 2022 in the Korean Intellectual Property Office, the disclosure of which is incorporated herein by reference.

BACKGROUND

1. Field

Embodiments of the present disclosure relate to an air cleaning and disinfection robot and a method of operating the same, and more particularly, to an air cleaning and disinfection robot and a method of operating the same that is capable of autonomously moving to an area in need of air cleaning or disinfection and performing air cleaning and disinfection operations.

2. Description of the Related Art

In modern society, is enjoying the convenience of life has improved and civilization has become richer with industrial development, but in return, human health is being fatally threatened by various harmful gases and fine dust. The World Health Organization (WTO has reported that the number of deaths due to air pollution has reached 3 million, among which the number of deaths due to indoor air is up to 93% of the total number of deaths, and there are research results showing that indoor air is predominantly affected by air pollution.

In this regard, an air cleaner has been developed to clean air by filtering out dust and germs in the air, and as the demand for a comfortable and clean living space or work-space has increased, the demand for air cleaners has been rapidly increasing.

A conventional air cleaner is manufactured to a predetermined specification or operation capacity and then supplied to a consumer, and the consumer positions the air cleaner in a specific indoor place for operation. However, since the size or shape of an indoor space in which the air cleaner is operated varies greatly, the operating efficiency of the air cleaner significantly decreases, and the air pollution levels are different for each area in the indoor space, which reduces the satisfaction of the consumer. In addition, a user needs to manually replace consumables such as a filter at regular intervals to maintain full functionality of the conventional air cleaner, but there is a problem in that frequent replacement of consumables is required in areas with high population density or high air pollution level.

Meanwhile, as human mobility gradually increases with the globalization of the world, harmful viruses are spreading rapidly with humans as intermediaries. Accordingly, social distancing measures are being practiced on national levels, and disinfection operations of periodically sanitizing or disinfecting individual homes or highly trafficked facilities are being practiced on individual or company levels.

In a conventional disinfection operation, a method in which a worker travels to an area that needs to be sanitized or disinfected and manually sprays chemicals while holding a tank where the chemicals are received is being mainly used. However, in addition to the potential adverse effect of the odor and residual substances of the chemicals on the health of the worker, there is a problem that it is difficult to manage a workforce in terms of time and cost because a large number of workers need to be secured.

SUMMARY

Therefore, it is an aspect of the present disclosure to provide an air cleaning and disinfection robot and a method of operating the same, which are capable of stably performing air cleaning and disinfection operations even in spaces having various sizes and shapes.

It is another aspect of the present disclosure to provide an air cleaning and disinfection robot and a method of operating the same, which are capable of improving the accuracy and efficiency of air cleaning and disinfection operations.

It is still another aspect of the present disclosure to provide an air cleaning and disinfection robot and a method of operating the same, which is capable of efficient operation by performing air cleaning and disinfection operations in a prioritized or selective manner in an area with a high pollution level.

It is yet another aspect of the present disclosure to provide an air cleaning and disinfection robot and a method of operating the same, in which a user can easily perform maintenance with a simple structure.

It is yet another aspect of the present disclosure to provide an air cleaning and disinfection robot and a method of operating the same, which can improve the utilization of indoor space by managing air in a large space with a single driving unit.

It is yet another aspect of the present disclosure to provide an air cleaning and disinfection robot and a method of operating the same, which can reduce a workforce and time required for managing air quality and cleanness.

Additional aspects of the disclosure will be set forth in part in the description which follows and, in part, will be obvious from the description, or may be learned by practice of the disclosure.

In accordance with one aspect of the present disclosure, an air cleaning and disinfection robot may include a driving unit configured to move autonomously in a target space, a plurality of air conditioning modules configured to manage air quality in the target space and detachably provided on the driving unit, a station on which the plurality of air conditioning modules are mounted, a docking unit configured to couple and separate the driving unit and each of the air conditioning modules to and from each other, and a detection unit configured to detect an operation environment of the target space, in which the driving unit, based on information obtained by the detection unit, may selectively couple to and move with any one of the plurality of air conditioning modules.

The station may be provided by including a main frame forming a body, and a plurality of mounting spaces formed inside the main frame to receive each of the plurality of air conditioning modules therein, and a mounting frame configured to support each of the air conditioning modules in each of the mounting spaces, and a plurality of detachable spaces, each formed at a lower side of the plurality of mounting spaces and provided such that the driving unit enters therein.

The docking unit may be provided by including a first docking member provided on a lower surface of each of the air conditioning modules and having a protrusion formed to protrude downwardly therefrom, a second docking member provided on an upper surface of the driving unit and having a seating portion into which the protrusion is inserted, and an elevating and lowering device provided on a side of the driving unit to elevate and lower the second docking member.

The docking unit may be provided by including a first docking member provided on a upper surface of each of the driving units and having a protrusion formed to protrude upwardly therefrom, a second docking member provided on a lower surface of each of the air conditioning modules and having a seating portion into which the protrusion is inserted, and an elevating and lowering device provided on a side of the driving unit to elevate and lower the first docking member.

A height between a floor surface of the target space and the lower surface of the air conditioning module elevated by the elevating and lowering device may be provided to be greater than a height between the floor surface of the target space and an upper end of the mounting frame.

Each of the air conditioning modules is supported by the pair of mounting frames facing each other, in which a maximum width of the second docking member and the elevating and lowering device may be provided to be smaller than a width of the pair of mounting frames facing each other.

The docking unit may be provided by further including a detachable portion provided between the protrusion and the seating portion.

The detachable portion may be provided by including a plurality of balls formed to protrude along an outer circumference of the protrusion and elastically supported, and a groove formed to be recessed along an inner circumference of the seating portion and into which at least a portion of the plurality of balls is inserted.

The detachable portion may be provided by further including at least one elastic member elastically supporting the plurality of balls.

The plurality of balls may be made of a magnetic material, and the detachable portion may further include an electromagnet configured to be supplied with power to cause the plurality of balls to protrude outside the protrusion or to be inserted inside the protrusion.

The protrusion may be formed in a cylindrical shape, and the seating portion may be formed to be hollow such that the protrusion is inserted therein and provided such that the first docking member and the second docking member are rotatable relative to each other.

The first docking member may be provided by including a first rotator provided with the protrusion and configured to be rotatable relative to the first docking member, and the second docking member may be provided by including a second rotator provided with the seating portion and configured to be rotatable relative to the second docking member.

The docking unit may be provided by further including at least one fastening pin formed to extend in an upward and downward direction in any one of the first rotator or the second rotator, and at least one fastening hole formed to be recessed in an upward and downward direction in the other of the first rotator or the second rotator and in which the fastening pin is inserted.

The first docking member may be provided by further including a first opening in which the first rotator is rotatably received, and the second docking member may be provided by further including a second opening in which the second rotator is rotatably received.

The elevating and lowering device may be provided by including a plurality of link members connected to the second docking member, in which adjacent link members are hinged to each other, and a docking drive unit configured to extend or shorten the plurality of link members in an upward or downward direction by rotating or moving at least one of the link members.

The elevating and lowering device may be provided by including a plurality of stretchable frames connected to the second docking member and provided to be insertable inside an adjacent frame, and a hydraulic cylinder connected to the stretchable frames and configured to extend or shorten the plurality of stretchable frames in an upward or downward direction.

The plurality of air conditioning modules may be provided by including at least one purification device configured to suction, purify, and discharge air of the target space, and at least one disinfection device configured to spray a disinfectant into the target space.

The detection unit may be provided by including an environmental recognition unit configured to recognize a surrounding environment of the target space by detecting at least one of a size, a shape, or an obstacle of the target space, and a pollution detection unit configured to detect an air pollution level in the target space.

Each of the purification devices may be provided by including a filter configured to filter out harmful substances, such as dust, included in the suctioned air, and wherein each of the disinfection devices includes a storage tank in which the disinfectant is received.

The air cleaning and disinfection robot may be provided by further including a controller configured to control operations of the air conditioning module, the driving unit, and the docking unit based on information obtained by the detection unit.

Each of the purification devices may be provided by including a first main body in which the filter is provided, and a discharge port through which the air purified through the filter is discharged, and each of the disinfection devices may be provided by including a second main body in which the storage tank is provided, and a spray port from which the disinfectant is sprayed.

The discharge port may be provided to be rotatable with respect to the first main body, and the spray port may be provided to be rotatable with respect to the second main body.

The discharge port may be provided to be able to be elevated or lowered with respect to the first main body, and the spray port may be provided to be able to be elevated or lowered with respect to the second main body.

The environmental recognition unit may be provided by including at least one of a distance sensor, a lidar sensor, an ultrasonic sensor, or an infrared sensor.

The pollution detection unit may be provided with at least one of a fine dust sensor, an ozone sensor, a carbon dioxide sensor, or a volatile organic compound sensor.

According to an operation method of the present embodiment, the controller may operate the driving unit to drive the purification device to enter the unoccupied mounting space, when a flow rate of air passing through a filter of any one of the purification devices is less than a preset flow rate, when an operating time of any one of the purification devices exceeds a preset time, or when an operation switch signal of a user occurs.

The controller may operate the driving unit to drive the purification device to enter the unoccupied mounting space, and then operate the docking unit to mount the purification device on the mounting frame and separate the driving unit from the purification device.

The controller may operate the driving unit to access and move to the mounting space in which the other one of the purification device in standby for operation or the disinfection device in standby for operation is mounted, after the driving unit and the purification device have been separated.

The controller may operate the docking unit to couple the driving unit to the other one of the purification device in standby for operation or the disinfection device in standby for operation, after the driving unit has accessed and moved to the mounting space in which the other one of the purification device in standby for operation or the disinfection device in standby for operation is mounted.

The controller may operate the docking unit to elevate the purification device from the driving unit before operating the driving unit to drive the purification device to enter the unoccupied mounting space.

The controller may operate the driving unit to drive the disinfection device to enter the unoccupied mounting space, when a level of disinfectant received in a storage tank of any one of the disinfection devices is lower than a preset level, when an operating time of any one of the disinfection devices exceeds a preset time, or when an operation switch signal of a user occurs.

The controller may operate the driving unit to drive the disinfection device to enter the unoccupied mounting space, and then operate the docking unit to mount the disinfection device on the mounting frame and separate the driving unit from the disinfection device.

The controller may operate the driving unit to access and move to the mounting space in which the other one of the disinfection device in standby for operation or the purification device in standby for operation is mounted, after the driving unit and the disinfection device have been separated.

The controller may operate the docking unit to couple the driving unit to the other one of the disinfection device in standby for operation or the purification device in standby for operation, after the driving unit has accessed and moved to the mounting space in which the other one of the disinfection device in standby for operation or the purification device in standby for operation is mounted.

The controller may operate the docking unit to elevate the disinfection device from the driving unit before operating the driving unit to drive the disinfection device to enter the unoccupied mounting space.

The controller may rotate the discharge port or the spray port based on information obtained by the environmental recognition unit and the pollution detection unit.

The controller may elevate the discharge port or the spray port based on information obtained by the environmental recognition unit and the pollution detection unit.

An air cleaning and disinfection robot and a method of operating the same according to the present embodiment can reliably perform air cleaning and disinfection operations in spite of spaces having various sizes and shapes.

An air cleaning and disinfection robot and a method of operating the same according to the present embodiment can improve the accuracy and efficiency of air cleaning and disinfection operations.

An air cleaning and disinfection robot and a method of operating the same according to the present embodiment can promote an efficient operation by performing air cleaning and disinfection operations in a prioritized or selective manner in an area with a high pollution level.

An air cleaning and disinfection robot and a method of operating the same according to the present embodiment can promote an easy maintenance of a user with a simple structure.

An air cleaning and disinfection robot and a method of operating the same according to the present embodiment can improve the utilization of indoor space by managing air in a large space with a single driving unit.

An air cleaning and disinfection robot and a method of operating the same according to the present embodiment can reduce a workforce and time required for managing air quality and cleanness.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Hereinafter, embodiments of the present disclosure will be described in detail with reference to the accompanying drawings. The embodiments below are presented to sufficiently convey the ideas of the present disclosure to those skilled in the art to which the present disclosure belongs. The present disclosure is not limited to the embodiments presented herein and may be specified as other forms. To clarify the present disclosure, the drawings may omit the illustration of parts that are not related to the description, and the size of components may be somewhat exaggerated for ease of understanding.

Figure 1:
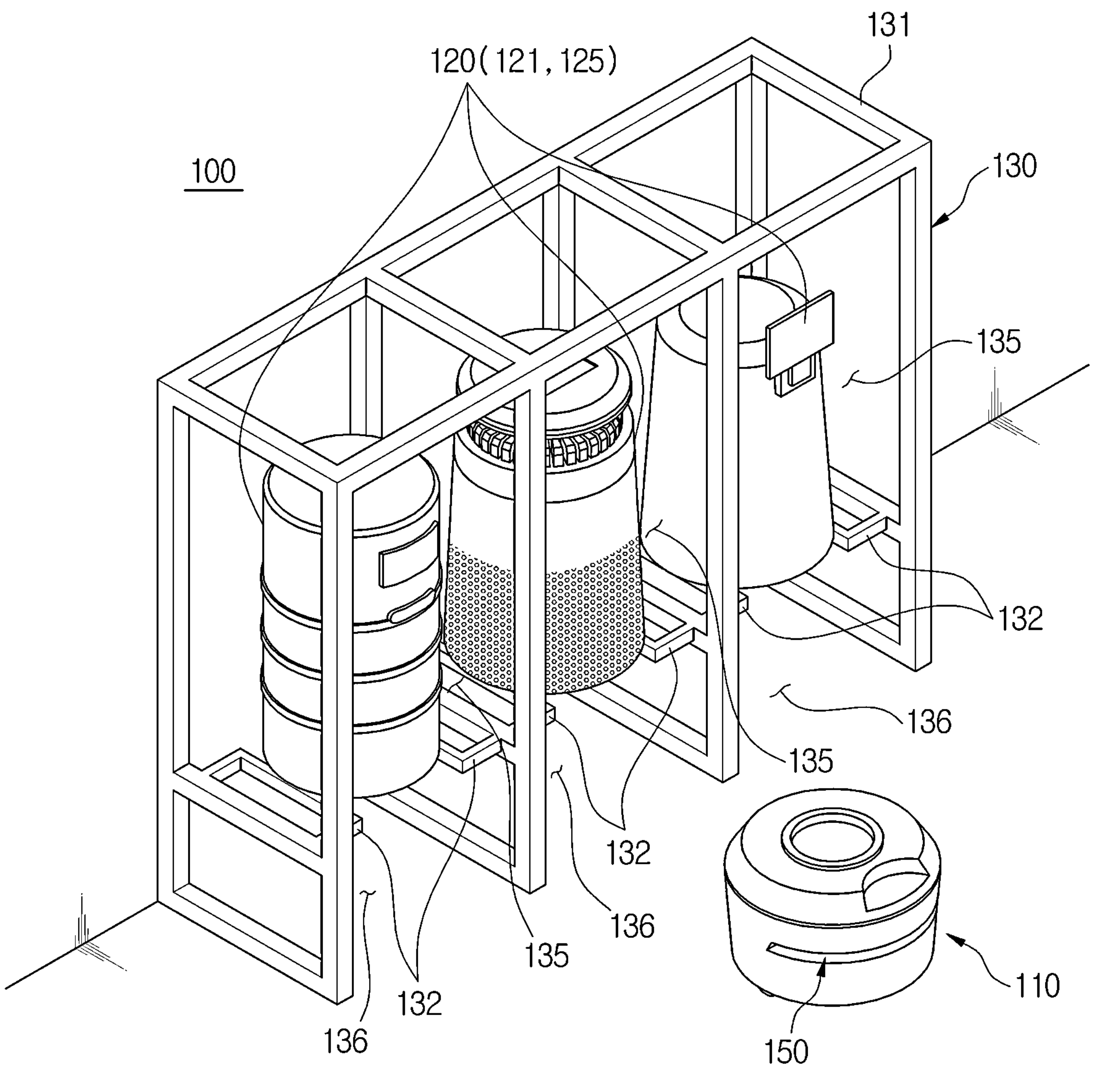
FIG. 1 is a perspective view illustrating an air cleaning and disinfection robot according to the present embodiment.
Figure 2:
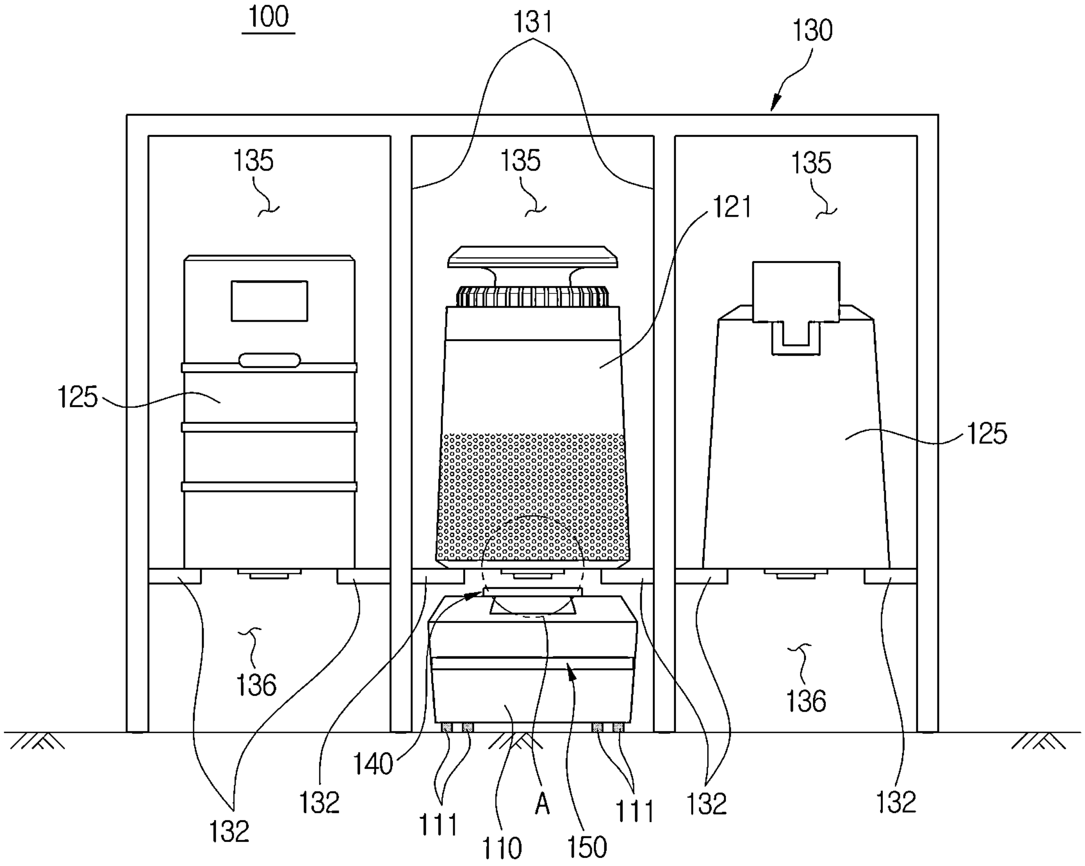
FIG. 2 is a side view illustrating the air cleaning and disinfection robot according to the present embodiment.

FIGS. 1 and 2 are perspective and side views, respectively illustrating an air cleaning and disinfection robot 100 according to the present embodiment.

Referring to FIGS. 1 and 2, the air cleaning and disinfection robot 100 according to the present embodiment includes a driving unit 110 configured to autonomously move in a target space to be air cleaned or disinfected, a plurality of air conditioning modules 120 configured to manage air quality in the target space, a station 130 in which the plurality of air conditioning modules 120 are in standby and mounted, a docking unit 140 configured to couple and separate the driving unit 110 and each of the air conditioning modules 120 from each other, a detection unit 150 configured to detect an operation environment of the target space, and a controller (not illustrated) configured to control an operation of a device based on information obtained by the detection unit 150.

The driving unit 110 is provided to enable autonomous driving on the target space, and may be coupled to and separated from the air conditioning module 120 by the docking unit 140 to be described below. The driving unit 110 may include a plurality of wheels 111 configured to perform a rolling motion along a floor surface of the target space, a driving motor (not illustrated) configured to drive and steer the plurality of wheels 111, and a housing forming an outer appearance and having the driving motor, the detection unit 150 to be described below, and a battery (not illustrated) received therein. The driving motor may generate rotational power by receiving power from a power source device such as a battery.

The plurality of wheels 111 are connected to an output shaft of the driving motor by a gear element and may perform a rotational motion by receiving power provided by the driving motor. The driving motor may be provided in plural and individually mounted on each wheel 111, and may implement steering of the driving unit 110 by varying an output of each driving motor, or may implement steering of the wheel 111 by separately having a steering device (not illustrated). The housing may be provided with a battery that supplies power to the driving motor, and may have the detection unit 150 and controller to be described below embedded therein, but may be provided with an opening on one side thereof through which a sensor of the detection unit 150 is exposed. In addition, the housing may be provided with a second docking member 144 of the docking unit 140 and an elevating and lowering device 149, and a detailed description thereof will be provided below.

The air conditioning module 120 may be provided to manage the air quality of the target space, and may be coupled to and separated from the driving unit 110 by the docking unit 140 to be described below. The air conditioning module 120 may be provided in plural and mounted and in standby at the station 130 to be described below, and the plurality of air conditioning modules 120 may include a purification device 121 configured to purify air in the target space and a disinfection device 125 configured to disinfect harmful viruses.

The purification device 121 may include a fan (not illustrated) rotationally operated to suction and discharge air from the target space, an electric motor (not illustrated) configured to operate the fan, a filter (not illustrated) configured to filter out dust or germs in the air transported by the fan, and a first main body having the fan, the electric motor, and the filter embedded therein, and a discharge port 122, which discharges air purified through the filter to the outside, may be provided on an upper side of the first main body to be capable of being rotated, and elevated or lowered with respect to the first main body. In addition, the disinfection device 125 may include a storage tank in which a disinfectant is received, a pump configured to suction and spray the disinfectant received in the storage tank, and a second main body having the storage tank and the pump embedded therein, and a spray port 126, through which the disinfectant is sprayed, may be provided on an upper side of the second main body to be capable of being rotated, and elevated or lowered with respect to the second main body.

Figure 8:
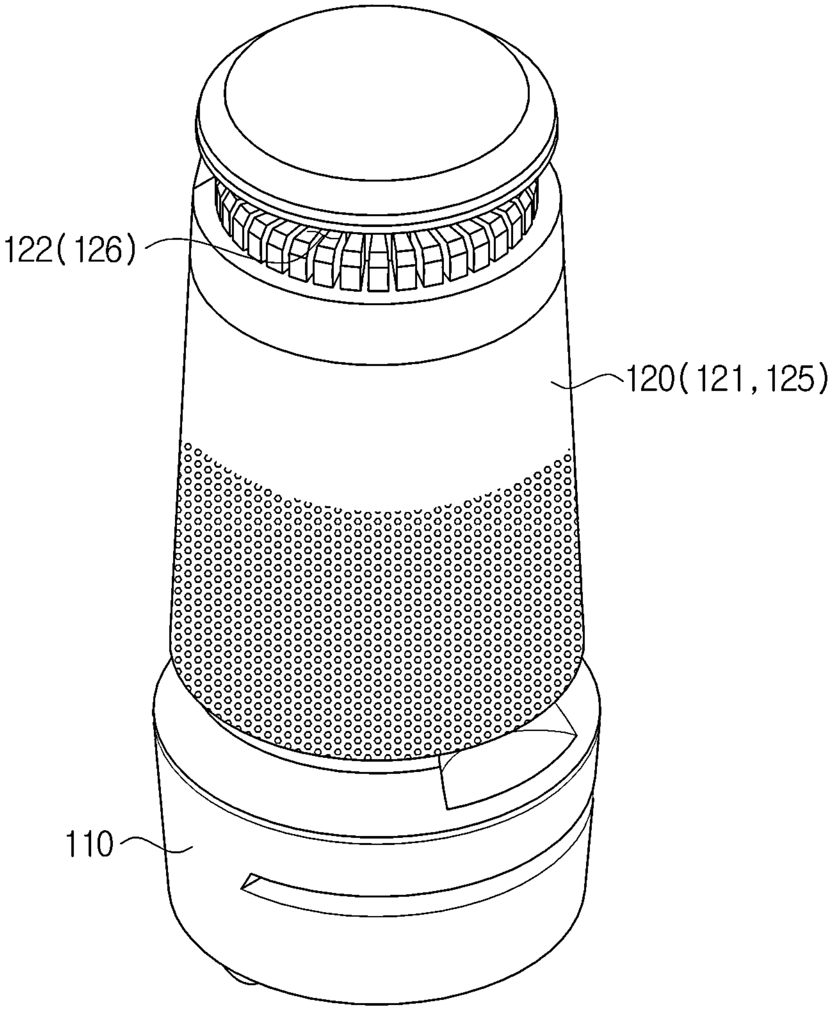
FIGS. 8 and 9 are perspective views illustrating a state in which a discharge port or a spray port of the air conditioning module rotates and is elevated or lowered, according to the present embodiment.
Figure 9:
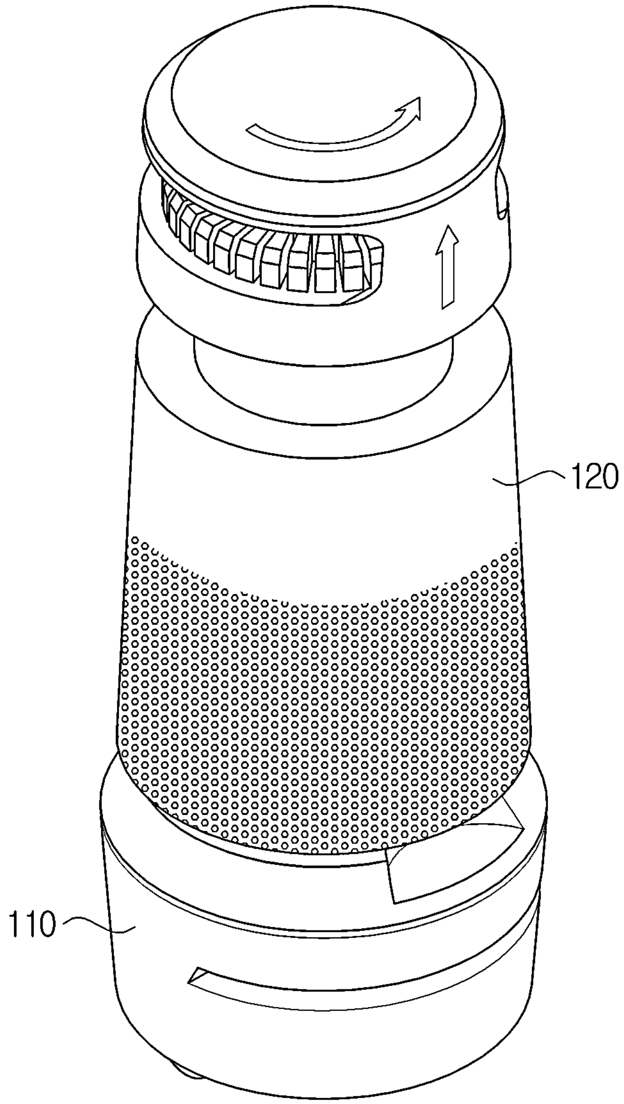
Figure 10:
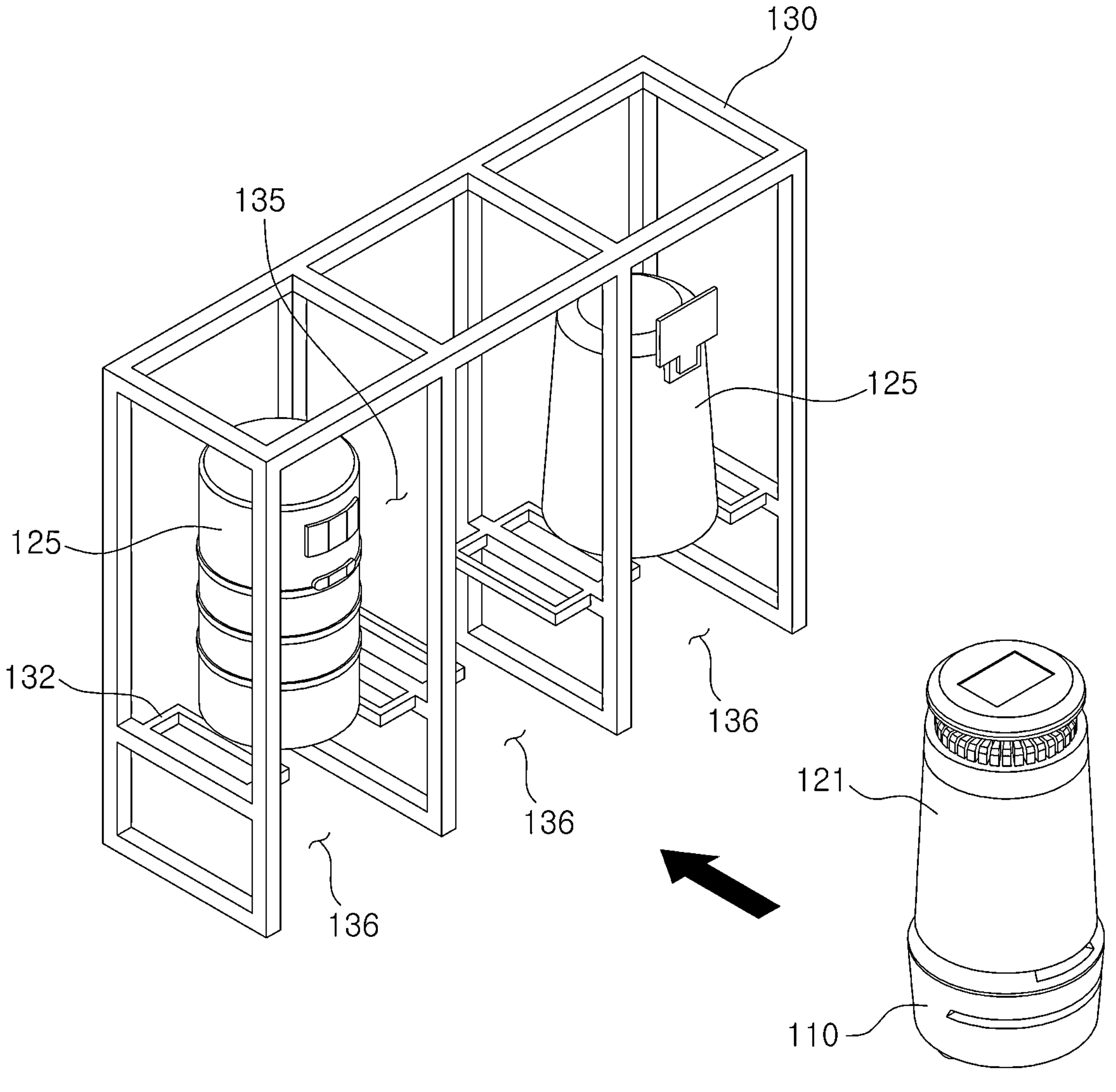
FIG. 10 is a perspective view illustrating a state in which the driving unit moves to a station for replacement of the air conditioning module, according to the present embodiment.

FIGS. 8 and 9 are perspective views illustrating a state in which the discharge port 122 or the spray port 126 of the air conditioning module 120 according to the present embodiment is rotated, and elevated or lowered, referring to FIG. 1, FIG. 2, FIG. 8, and FIG. 9, the discharge port 122 of the purification device 121 and the spray port 126 of the disinfection device 125 may be rotated, and elevated or lowered to efficiently and quickly perform air purification or disinfection operations based on information obtained by the detection unit 150 to be described below. In an example, the discharge port 122 of the purification device 121 may be rotated toward a dusty area on the target space. When there are many obstacles in the target space and thus it is difficult for the driving unit 110 to access the target space, the discharge port 122 of the purification device 121 may perform a purification operation in an elevated state.

Similarly, the spray port 126 of the disinfection device 125 may be rotated toward an area with a large number of harmful viruses in the target space. When there are many obstacles in the target space and thus it is difficult for the driving unit 110 to access the target space, the spray port 126 of the disinfection device 125 may perform a disinfection operation in an elevated state. Further, when purification or disinfection over a large target area is desired, after the air conditioning module 120 has been moved by the driving unit 110 in close proximity to a wall or pillar, the discharge port 122 or the spray port 126 may be operated in a state of being rotated and elevated in a direction facing away from the wall or pillar.

Although not illustrated in the drawings, the discharge port 122 of the purification device 121 and the spray port 126 of the disinfection device 125 may be rotationally operated with respect to the first main body and the second main body by an electric device, a rack-and-pinion gear device, or the like, and also may be operated to be elevated and lowered with respect to the first main body and the second main body by a foldable link, a hydraulic cylinder, or the like. However, this is an example to assist in the understanding of the present disclosure and the present disclosure is not limited thereto, and as long as the discharge port 122 or the spray port 126 can be rotated, and elevated or lowered with respect to the main body, this may of course be achieved by devices of various structures.

A first docking member 141 of the docking unit 140, which will be described below, is provided on a lower side of each of the purification device 121 and the disinfection device 125, and may be coupled to a second docking member 144 exposed on an upper side of the driving unit 110, and a detailed description thereof will be provided below.

The station 130 is provided for the plurality of air conditioning modules 120 to be in standby and mounted. The station 130 may include a main frame 131 forming a body, a plurality of mounting spaces 135 formed inside the main frame 131 and in which each air conditioning module 120 is received, a detachable space 136 formed at a lower side of each of the mounting spaces 135 and provided such that the driving unit 110 may enter, and a mounting frame 132 provided between the mounting space 135 and the detachable space 136 to support a lower end of each of the air conditioning modules 120.

The main frame 131 has a plurality of frames formed to extend in a leftward and rightward direction, an upward and downward direction, and a width direction with respect to FIG. 2, and ends thereof are connected to each other to form a lattice shape, thus rigidity can be secured. Inside the main frame 131, there may be provided the plurality of mounting spaces 135 in which the plurality of air conditioning modules 120 are received to be in standby before operation or to return after operation, and the detachable space 136 provided at a lower side of each mounting space 135 in which the driving unit 110 may enter. There may be provided a pair of mounting frames 132 between each of the mounting spaces 135 and the detachable space 136 to support and mount the air conditioning module 120 received in the mounting space 135. Each of the mounting frames 132 may be formed to protrude inwardly so that a lower end or a lower surface of the air conditioning module 120 may be caught and supported on an upper end of the mounting frame 132.

The mounting frame 132 may be provided such that a height from a floor surface of the target space to a lower end of the air conditioning module 120 elevated by the docking unit 140 may be greater than a height from the floor surface of the target space to an upper end of the mounting frame 132, so as to stably and easily mount the air conditioning module 120 that has entered the mounting space 135 by the driving unit 110. In addition, in order to allow the docking unit 140 to be described below to operate smoothly inside the pair of mounting frames 132, a width or spacing between the pair of mounting frames 132 may be provided greater than a maximum width of the second docking member 144 of the docking unit 140 and the elevating and lowering device 149.

The docking unit 140 is provided to couple and separate the driving unit 110 and each of the air conditioning modules 120 to and from each other.

Figure 3:
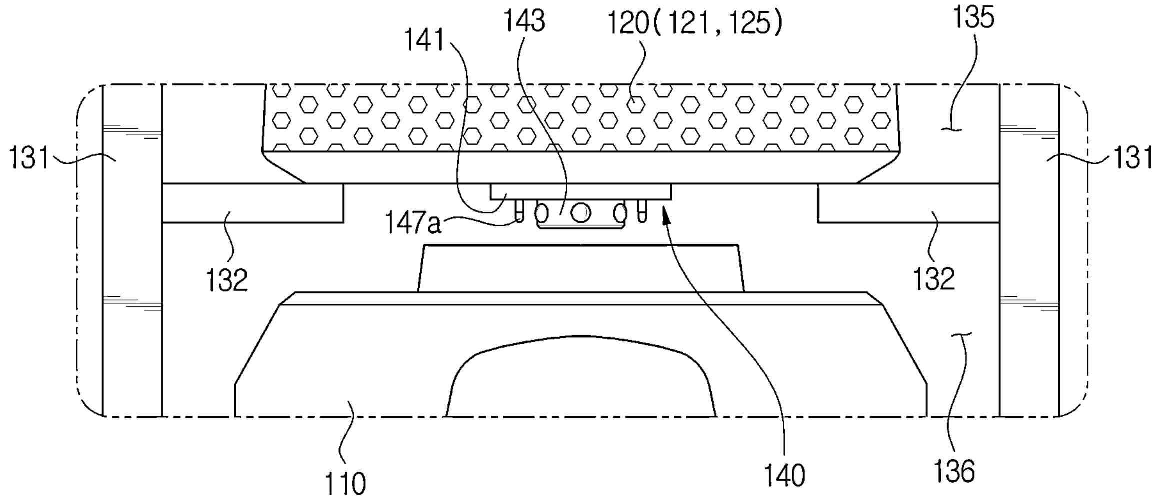
FIG. 3 is an enlarged view of portion A of FIG. 2, illustrating a state in which a driving unit and an air conditioning module are separated according to the present embodiment.
Figure 4:
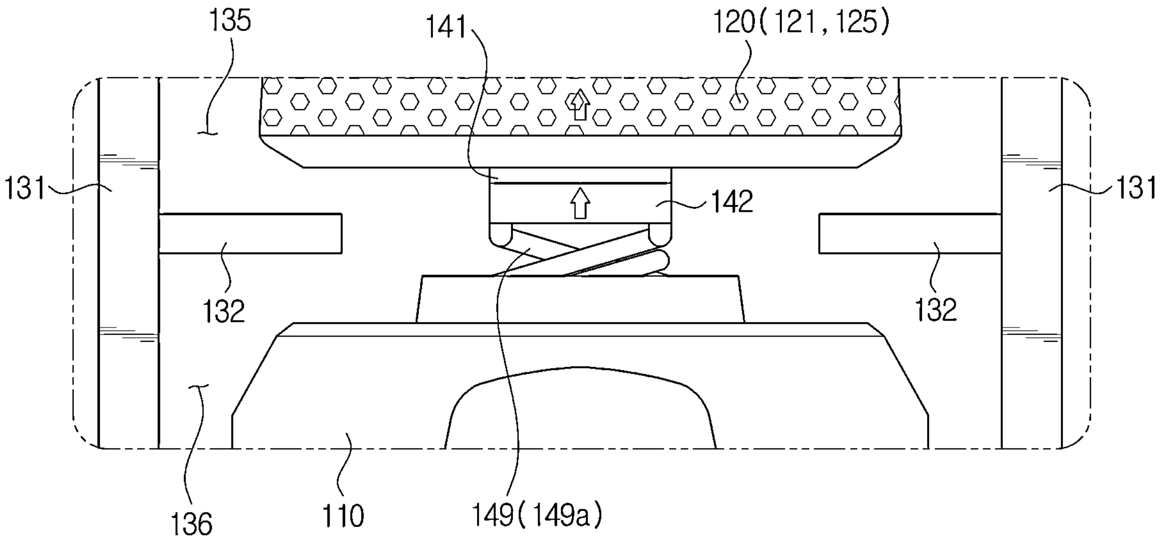
FIG. 4 is an enlarged view of portion A of FIG. 2, illustrating a state in which the driving unit and the air conditioning module are in close proximity to each other by a docking unit according to the present embodiment.
Figure 5:
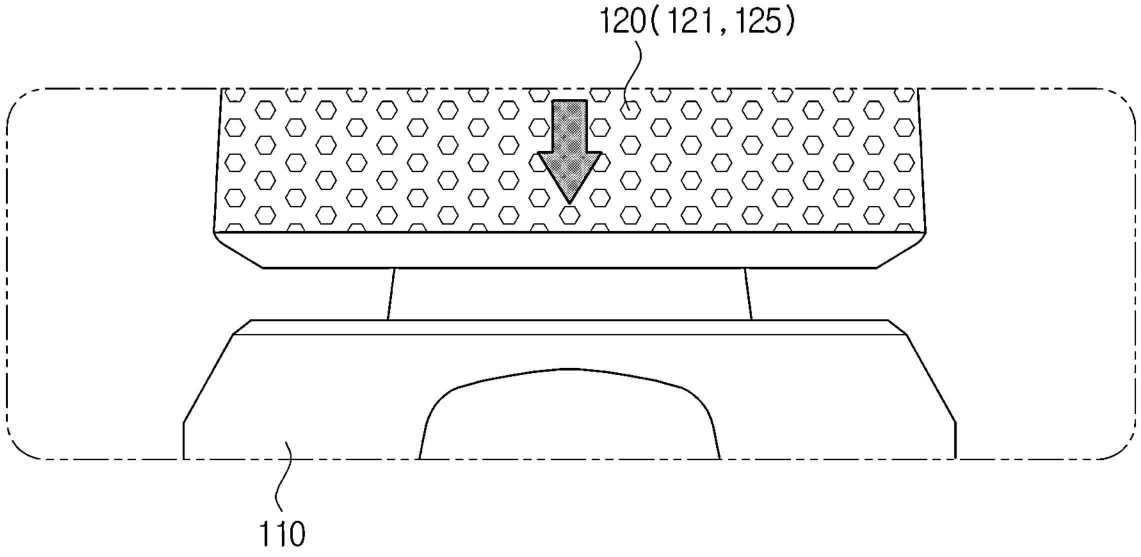
FIG. 5 is an enlarged view of portion A of FIG. 2, illustrating a state in which the driving unit and the air conditioning module are coupled by the docking unit according to the present embodiment.
Figure 6:
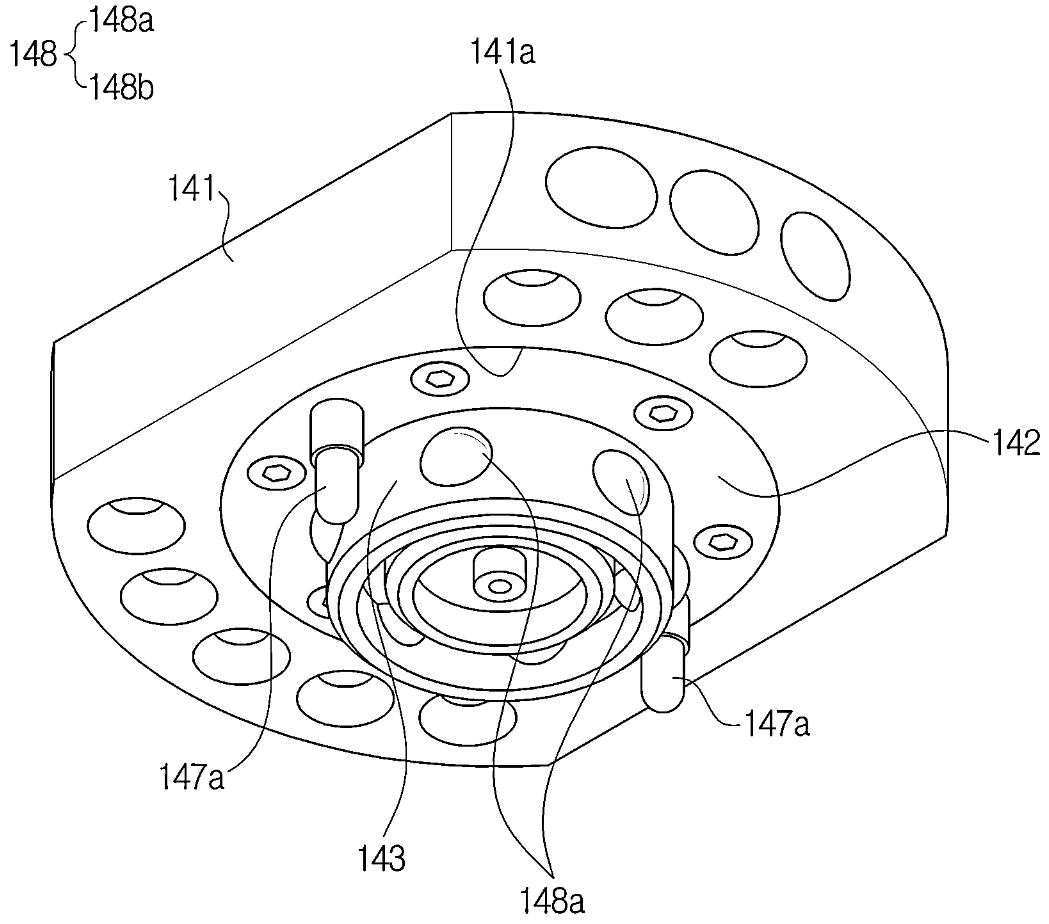
FIG. 6 is a perspective view illustrating a first docking member of the docking unit according to the present embodiment.
Figure 7:
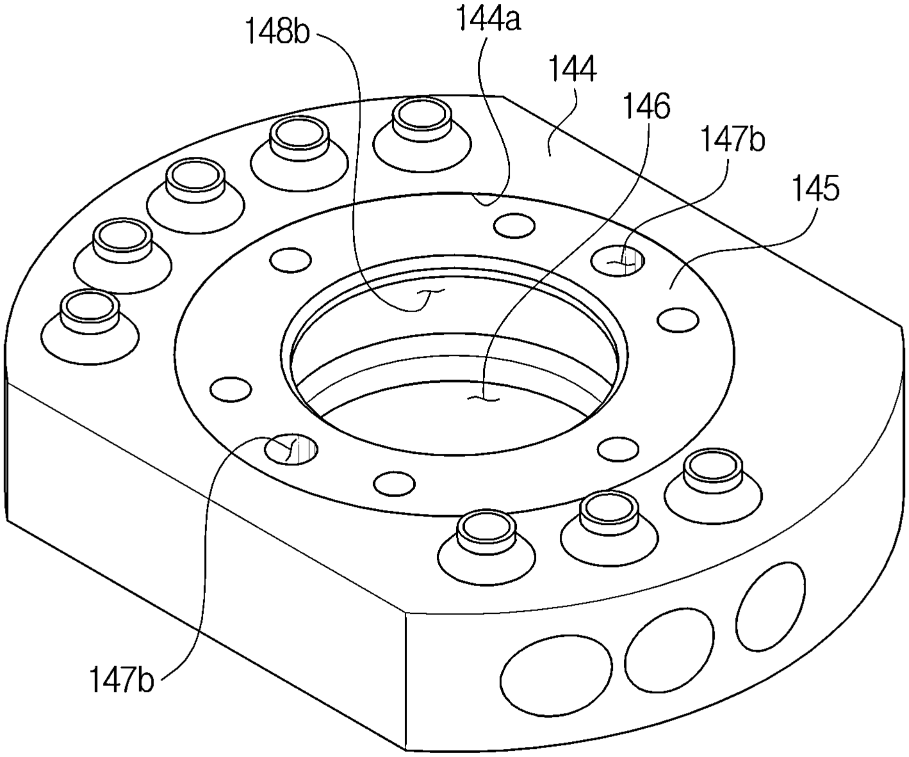
FIG. 7 is a perspective view illustrating a second docking member of the docking unit according to the present embodiment.

FIGS. 3 to 5 are enlarged views of portion A of FIG. 2, FIG. 3 illustrates a state in which the driving unit 110 and the air conditioning module 120 are separated, FIG. 4 illustrates a state in which the driving unit 110 and the air conditioning module 120 are in close proximity to each other by the docking unit 140, and FIG. 5 illustrates a state in which the driving unit 110 and the air conditioning module 120 are coupled by the docking unit 140. In addition, FIG. 6 is a perspective view illustrating the first docking member 141 of the docking unit 140 according to the present embodiment, and FIG. 7 is a perspective view illustrating the second docking member 144 of the docking unit 140 according to the present embodiment.

Referring to FIGS. 3 to 7, the docking unit 140 may include the first docking member 141 having a protrusion 143 provided on a lower side of each of the air conditioning modules 120 and formed to protrude therefrom, the second docking member 144 provided on an upper side of the driving unit 110 and having a seating portion 146 into which the protrusion 143 is inserted, a detachable portion 148 provided between the protrusion 143 and the seating portion 146, and the elevating and lowering device 149 provided on the driving unit 110 to elevate and lower the air conditioning module 120.

The first docking member 141 is provided on a lower surface of each air conditioning module 120, and is in contact with and coupled to the second docking member 144, which is provided on the driving unit 110. The first docking member 141 may be provided to be externally exposed on the lower surface of the air conditioning module 120, and the first docking member 141 provided on the air conditioning module 120 may be provided to be rotatable relative to the second docking member 144 provided on the driving unit 110 so that the air conditioning module 120 can rotate freely with respect to the driving unit 110. To this end, the first docking member 141 may include a first rotator 142 formed in the shape of a disk, and a first opening 141*a* formed to be hollow therein to rotatably receive the first rotator 142. There may be provided the protrusion 143 formed to protrude downwardly on a lower surface of the first rotator 142, and the protrusion 143 may also be formed in the shape of a disk, and a plurality of balls 148*a* of the detachable portion 148 may be formed to protrude along an outer circumferential surface of the protrusion 143.

The second docking member 144 is provided on the upper surface of the driving unit 110, and is in contact with and coupled to the first docking member 141, which is provided on each of the air conditioning modules 120. The second docking member 144 may be provided to be externally exposed on the upper surface of the driving unit 110, and may be connected to the elevating and lowering device 149 to be elevated and lowered. In addition, the second docking member 144 may be provided with the seating portion 146 into which the protrusion 143 provided in the first docking member 141 is inserted, and the seating portion 146 may be formed to be recessed or hollow with a shape corresponding to a shape of the protrusion 143. The second docking member 144 may be provided with a second rotator 145 that is formed in the shape of a disk so that the air conditioning module 120 may rotate freely with respect to the driving unit 110 and has the seating portion 146 formed to be hollow in a center thereof into which the protrusion 143 is inserted, and a second opening 144*a* that is formed to be hollow to rotatably receive the second rotator 145 therein. The seating portion 146 may have a groove 148*b* formed to be recessed along an inner circumferential surface thereof to allow the balls 148*a* of the detachable portion 148 to be inserted and moved.

The elevating and lowering device 149 is provided to elevate and lower the second docking member 144. The elevating and lowering device 149 may include a plurality of link members 149*a* rotatably connected to the second docking member 144 and hinged to each other, and a docking drive unit (not illustrated) mounted to the driving unit 110 to rotate or move at least one of the link members 149*a* to extend or shorten the plurality of link members 149*a* in an upward and downward direction. The plurality of link members 149*a* may be hinged at both ends to neighboring link members 149*a*, and an uppermost link member 149*a* may be rotatably connected to the second docking member 144 and a lowermost link member 149*a* may be connected to the docking drive unit. The docking drive unit may include a rack gear formed to extend along a lengthwise direction of the link members 149*a*, an electric motor, and a pinion gear connected to an output shaft of the electric motor and a hinge shaft of the lowermost link member 149*a*. Therefore, as the electric motor operates in both directions, the pinion gear moves along the rack gear, causing the link members 149*a* to be extended or shortened in an upward or downward direction, thus allowing the second docking member 144 to be elevated or lowered.

In addition to this, the elevating and lowering device 149 may be configured with various manner of structures and devices. In an example, the elevating and lowering device 149 may include a plurality of stretchable frames provided to be insertable into an adjacent frame, and a docking drive unit having one end connected to the stretchable frames and the other end connected to a side of the driving unit 110 to extend or shorten the plurality of stretchable frames in an upward or downward direction. The plurality of stretchable frames may be formed with a hollow interior, and may be provided in a telescopic structure in which a diameter or a size of an interior space of the stretchable frames is gradually increased or decreased as the stretchable frames is shortened by insertion of one side of the stretchable frames into the other side of the stretchable frames, and extended by protrusion. The docking drive unit may be provided with a hydraulic cylinder having one end connected to and supported by the stretchable frames and the other end supported on a housing side of the driving unit 110. Through this, the hydraulic cylinder may be expanded or contracted to extend or shorten the stretchable frames in an upward and downward direction, thereby elevating or lowering the second docking member 144.

The detachable portion 148 is provided between the protrusion 143 and the seating portion 146 to promote easy coupling between the first docking member 141 and the second docking member 144, and to maintain a stable coupling state. The detachable portion 148 may include the plurality of balls 148*a* formed to protrude along an outer circumference of the protrusion 143, and the groove 148*b* formed to be recessed along an inner circumference of the seating portion 146. At least a portion of the plurality of balls 148*a* may protrude outwardly through an opening formed in an outer circumference of the protrusion 143, and the plurality of balls 148*a* may be disposed to be spaced apart from each other at a predetermined distance.

The plurality of balls 148*a* may be elastically supported on the protrusion 143. To this end, the plurality of balls 148*a* may be elastically supported outwardly by an elastic member, and when the protrusion 143 is inserted into the seating portion 146, the first docking member 141 and the second docking member 144 may be easily coupled by the plurality of balls 148*a* contacting an entrance of the seating portion 146, being inserted inwardly, and then protruding and being inserted again toward the groove 148*b*. As such, the first docking member 141 and the second docking member 144 can be coupled and maintained with each other by the plurality of balls 148*a* on which the detachable portion 148 is elastically supported and the groove 148*b* into which the balls 148*a* are received, thereby implementing quick and easy coupling and separation of the air conditioning module 120 and the driving unit 110. Meanwhile, in contrast, the plurality of balls 148*a* may be made of a magnetic material and an electromagnet may be provided inside the protrusion 143, such that the plurality of balls 148*a* may be protruded and inserted by an electrical signal applied to the electromagnet.

The docking unit 140 may further include at least one fastening pin 147*a* and an fastening hole 147*b* for stable coupling between the first rotator 142 and the second rotator 145. The fastening pin 147*a* may be formed to protrude and extend on any one of the first rotator 142 or the second rotator 145 in an upward and downward direction, and the fastening hole 147*b* may be formed to be recessed in the other one of the first rotator 142 or the second rotator 145 in an upward and downward direction such that the fastening pin 147*a* may be inserted. FIGS. 6 and 7 illustrate that the fastening pin 147*a* is provided on the first rotator 142 and the fastening hole 147*b* is provided in the second rotator 145. However, it is of course possible that the fastening pin 147*a* is provided on the second rotator 145 and the fastening hole 147*b* is provided in the first rotator 142. The first rotator 142 and the second rotator 145 can be stably coupled to each other through the fastening pin 147*a* and the fastening hole 147*b*, and the driving unit 110 and the air conditioning module 120 can implement stable operation without any clearance from each other.

Briefly describing an operation of the docking unit 140, when the driving unit 110 and the air conditioning module 120 intend to couple to each other, the driving unit 110 enters the detachable space 136 at the lower side of the mounting space 135 where the air conditioning module 120 to be operated is in standby (see FIG. 3), and the second docking member 144 to be described below is elevated by the elevating and lowering device 149 of the docking unit 140 to couple to the first docking member 141 of the air conditioning module 120, and the air conditioning module 120 is spaced apart and elevated from the mounting frame 132 (see FIG. 4). Then, after the driving unit 110 and the air conditioning module 120 are departed from the detachable space 136 and the mounting space 135, the second docking member 144 is lowered by the elevating and lowering device 149 so that the driving unit 110 and the air conditioning module 120 can be coupled (see FIG. 5).

In contrast, when the driving unit 110 and the air conditioning module 120 intend to be separated, after the driving unit 110 and the air conditioning module 120 approach the unoccupied mounting space 135 on the main frame 131, the second docking member 144 is elevated by the elevating and lowering device 149 to elevate the air conditioning module 120 from the driving unit 110 before the driving unit 110 and the air conditioning module 120 enter the detachable space 136 and the mounting space 135. Then, the driving unit 110 and the air conditioning module 120 enter the detachable space 136 and the mounting space 135, and the second docking member 144 is lowered by the elevating and lowering device 149, so that the air conditioning module 120 is caught, supported, and mounted on the mounting frame 132, and simultaneously the driving unit 110 and the air conditioning module 120 can be separated.

Meanwhile, FIGS. 3 to 7 illustrate and describe that the first docking member 141 having the protrusion 143 is provided on the lower surface of the air conditioning module 120, and the second docking member 144 having the seating portion 146 is provided on the upper surface of the driving unit 110, but the present disclosure is not limited thereto, and it may be equally understood even when the first docking member 141 is provided on the upper surface of the driving unit 110, and the protrusion 143 is formed to protrude upwardly, and the second docking member 144 having the seating portion 146 is provided on the lower surface of each of the air conditioning modules 120, and the elevating and lowering device 149 elevates and lowers the first docking member 141 to enable the driving unit 110 and the air conditioning module 120 to be coupled and separated.

The detection unit 150 is provided to detect and recognize an operation environment of the target space. The detection unit 150 may be mounted inside the driving unit 110 and may detect the operation environment through an opening formed on one side of the housing. The detection unit 150 may include an environmental recognition unit configured to recognize a surrounding environment of the target space, such as a size, a shape, and obstacles of the target space, and a pollution detection unit configured to detect an air pollution level caused by dust, harmful viruses, and the like included in the air of the target space.

The environmental recognition unit may include at least one of a distance sensor, a lidar sensor, an ultrasonic sensor, or an infrared sensor to detect various obstacles present in the target space, and the pollution detection unit may include at least one of a fine dust sensor, an ozone sensor, a carbon dioxide sensor, or a volatile organic compound sensor to detect various harmful substances present in the air of the target space. However, this is an example to assist in the understanding of the present invention, and it is of course understood that various types of sensors may be employed as long as they are capable of detecting the operation environment of the target space. The environmental recognition unit and the pollution detection unit may transmit the detected and recognized information to the controller, and the controller may control operations of the driving unit 110, the air conditioning module 120, and the docking unit 140 based on the information obtained by the environmental recognition unit and the pollution detection unit.

Hereinafter, a method of operating the air cleaning and disinfection robot 100 according to the present embodiment will be described.

FIGS. 10 to 15 are perspective views illustrating an operation of the air cleaning and disinfection robot 100 according to the present embodiment in sequence. With reference thereto, while the purification device 121 and the driving unit 110 are coupled to perform an operation of purifying the air in the target space, when it is determined that a replacement of the filter is necessary because a flow rate of the air passing through the filter is lower than a preset flow rate, when it is determined that a sufficient purification operation has been performed because an operating time of the purification device 121 exceeds a preset time, or when an operation switch signal is received from a user, the controller allows the driving unit 110 to approach toward the unoccupied mounting space 135 and detachable space 136 on the station 130 (see FIG. 10).

Figure 11:
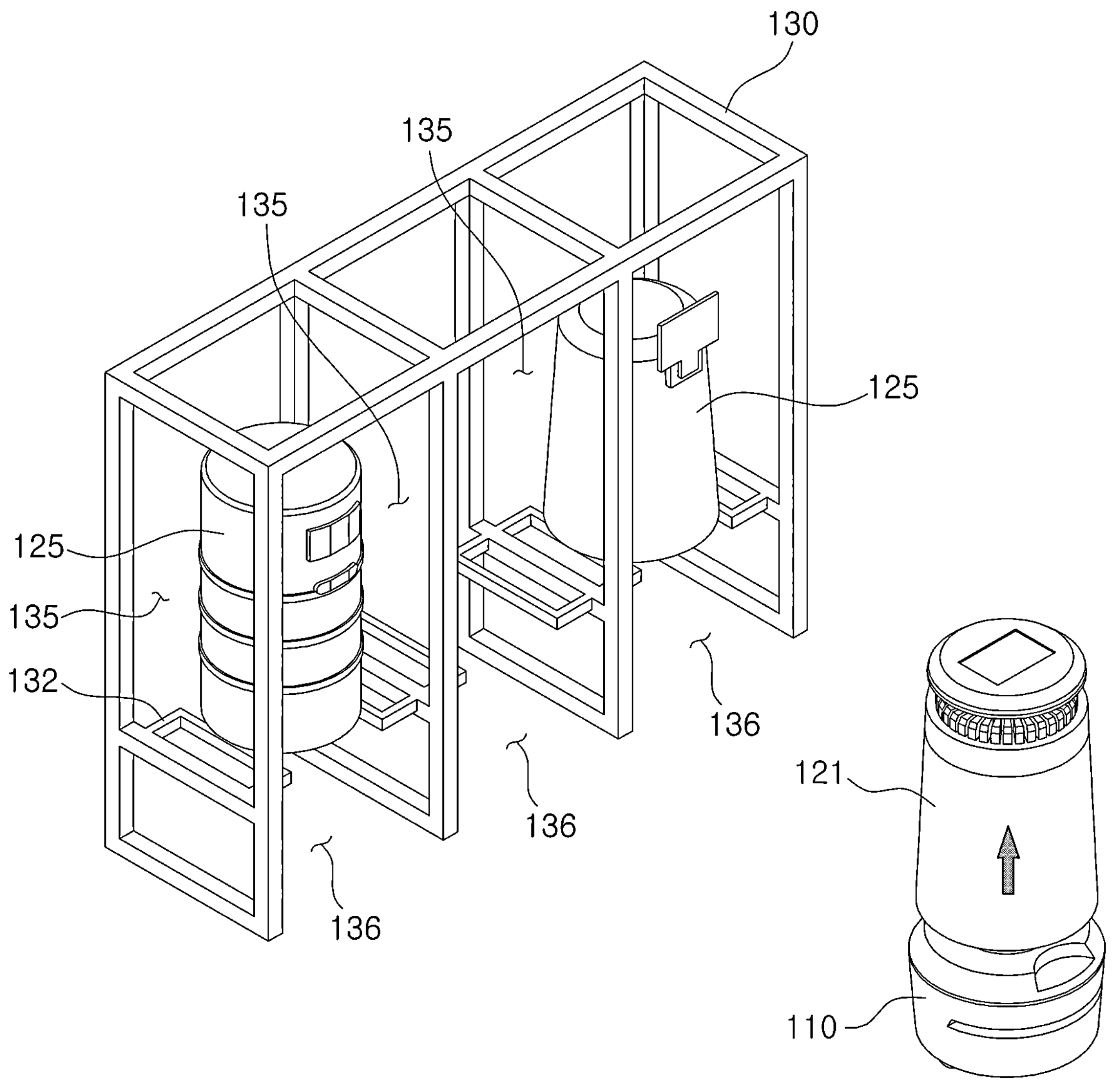
FIG. 11 is a perspective view illustrating a state in which the air conditioning module is elevated from the driving unit by the docking unit, according to the present embodiment.
Figure 12:
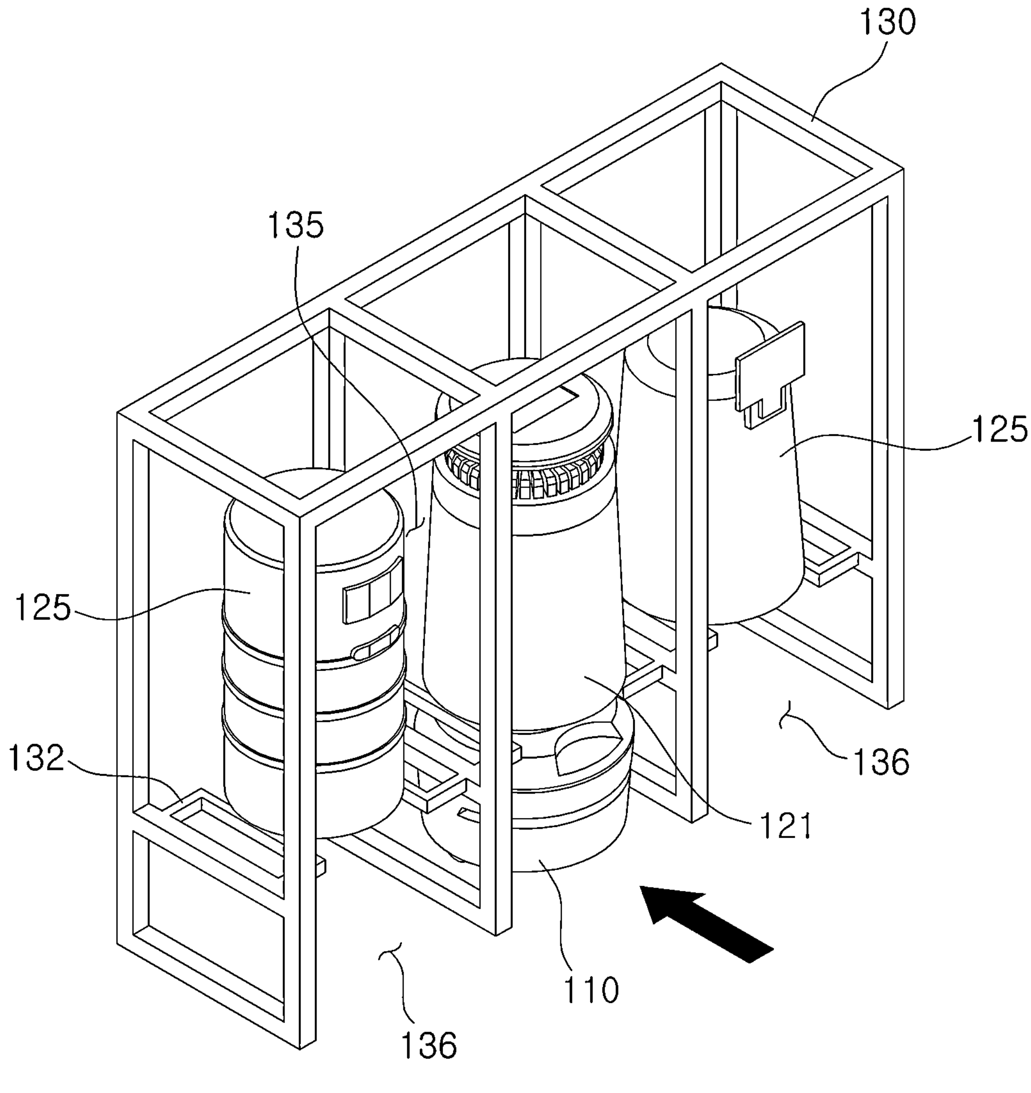
FIG. 12 is a perspective view illustrating a state in which the driving unit and the air conditioning module have entered an unoccupied mounting space of the station, according to the present embodiment.

Before the purification device 121 and the driving unit 110 enter the unoccupied mounting space 135 and detachable space 136, the controller operates the elevating and lowering device 149 of the docking unit 140 to elevate the purification device 121 from the driving unit 110 so that the purification device 121 can stably enter and be mounted in the mounting space 135 on the upper side of the mounting frame 132 (see FIG. 11).

Figure 13:
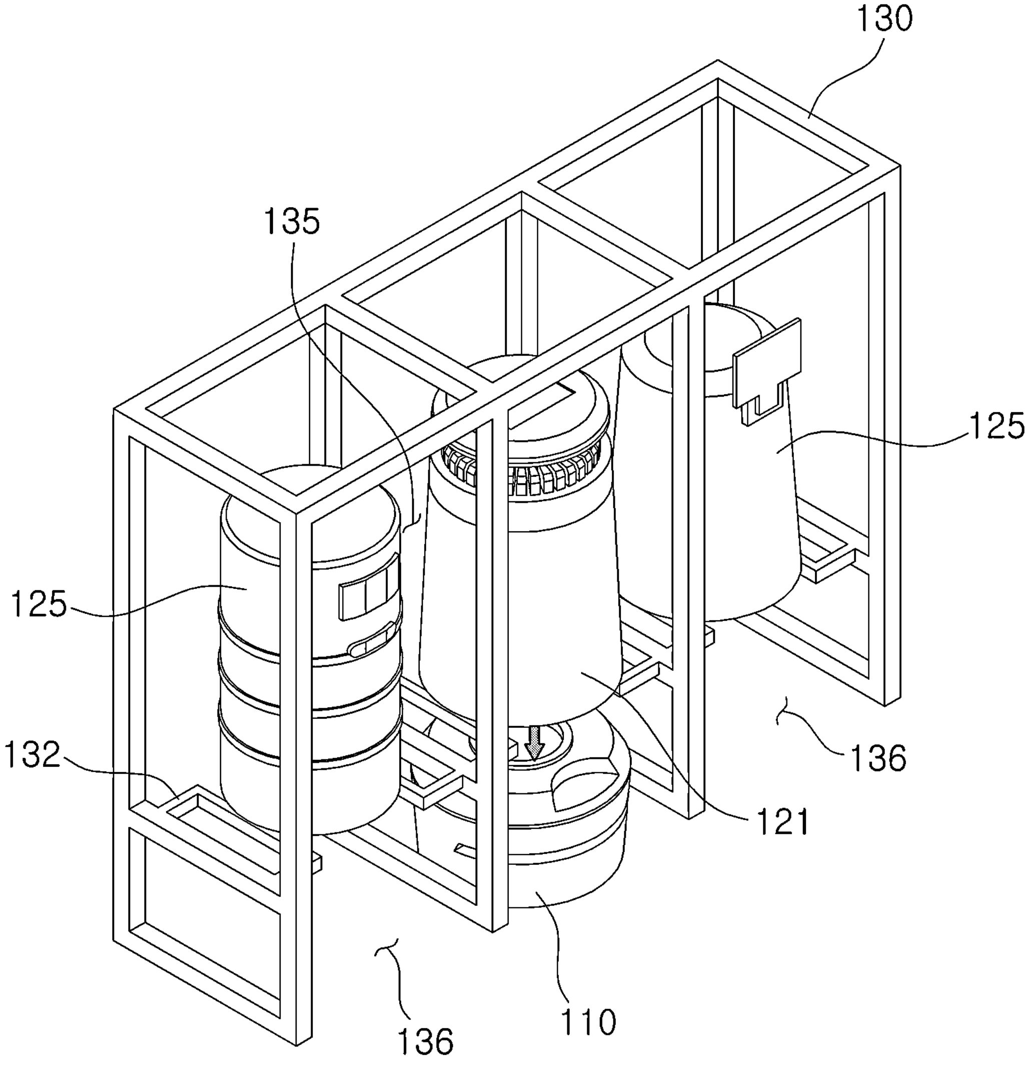
FIG. 13 is a perspective view illustrating a state in which the air conditioning module is separated from the driving unit by the docking unit and mounted on the station, according to the present embodiment.
Figure 14:
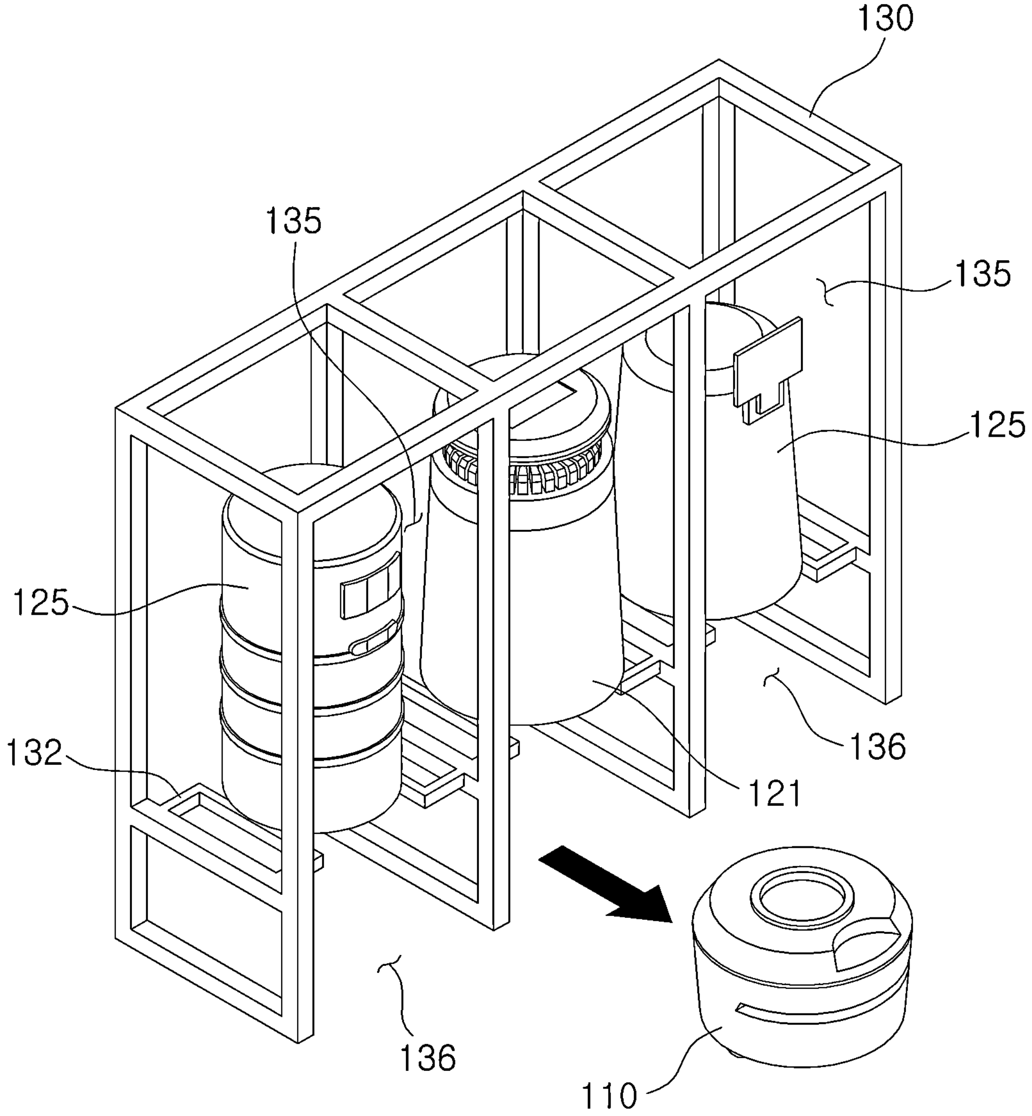
FIG. 14 is a perspective view illustrating a state in which the driving unit is separated from the air conditioning module to be replaced and then departed from a detachable space, according to the present embodiment.
Figure 15:
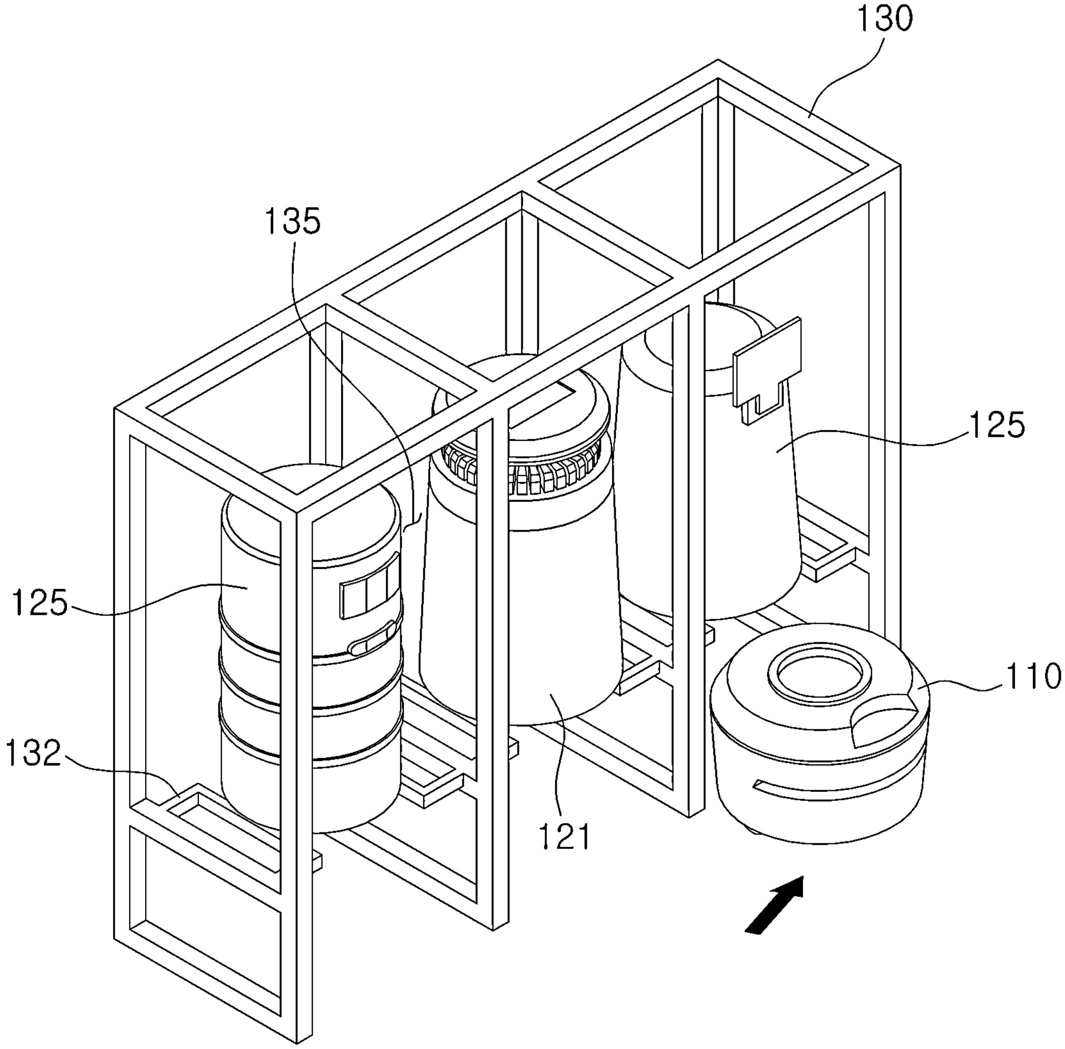
FIG. 15 is a perspective view illustrating a state in which the driving unit is entering the detachable space at a lower side of the mounting space in which the air conditioning module to be coupled and operated is mounted, according to the present embodiment.

With the purification device 121 elevated from the driving unit 110 by the docking unit 140, the controller allows the driving unit 110 to enter the unoccupied mounting space 135 and detachable space 136 (see FIG. 12), and operates the elevating and lowering device 149 of the docking unit 140 to lower the second docking member 144, thereby mounting the purification device 121 on the mounting frame 132 and simultaneously separating the driving unit 110 from the purification device 121 (see FIG. 13).

Then, the controller may operate the driving unit 110 to be departed from the corresponding detachable space 136 (see FIG. 14), and allow the driving unit 110 to access and move into the detachable space 136 at the lower side of the mounting space 135 where the disinfection device 125 in standby for operation is mounted (see FIG. 15), and again, the controller may operate the elevating and lowering device 149 of the docking unit 140 to couple the disinfection device 125 in standby for operation to the driving unit 110 so that subsequent operations can proceed continuously without delays due to maintenance.

The same above may be applied to an operation after the disinfection device 125 and the driving unit 110 are coupled to perform a disinfection operation of the target space.

While the disinfection device 125 and the driving unit 110 are coupled to perform an operation to disinfect harmful viruses in the target space, when it is determined that the replenishment of the disinfectant or the replacement of the disinfection device 125 is necessary because a level of the disinfectant received in the storage tank of the disinfection device 125 is lower than a preset level, when it is determined that a sufficient disinfection operation has been performed because an operating time of the disinfection device 125 exceeds a preset time, or when an operation switch signal is received from a user, the controller allows the driving unit 110 to approach toward the unoccupied mounting space 135 and detachable space 136 on the station 130.

Before the disinfection device 125 and the driving unit 110 enter the unoccupied mounting space 135 and detachable space 136, the controller operates the elevating and lowering device 149 of the docking unit 140 to elevate the disinfection device 125 from the driving unit 110 so that the disinfection device 125 can stably enter and be mounted in the mounting space 135 at the upper side of the mounting frame 132.

With the disinfection device 125 elevated from the driving unit 110 by the docking unit 140, the controller allows the driving unit 110 to enter the unoccupied mounting space 135 and detachable space 136, and operates the elevating and lowering device 149 of the docking unit 140 to lower the second docking member 144, thereby mounting the disinfection device 125 on the mounting frame 132 and simultaneously separating the driving unit 110 from the disinfection device 125.

Then, the controller may operate the driving unit 110 to be departed from the corresponding detachable space 136, and allow the driving unit 110 to access and move to the detachable space 136 at the lower side of the mounting space 135 where the disinfection device 125 or the purification device 121 in standby for operation is mounted, and may operate the elevating and lowering device 149 of the docking unit 140 to couple the disinfection device 125 or the purification device 121 in standby for operation to the driving unit 110 to perform subsequent operations in succession.

Hereinafter, an operation of the discharge port 122 or the spray port 126 of the air conditioning module 120 according to the present embodiment will be described.

Figure 16:
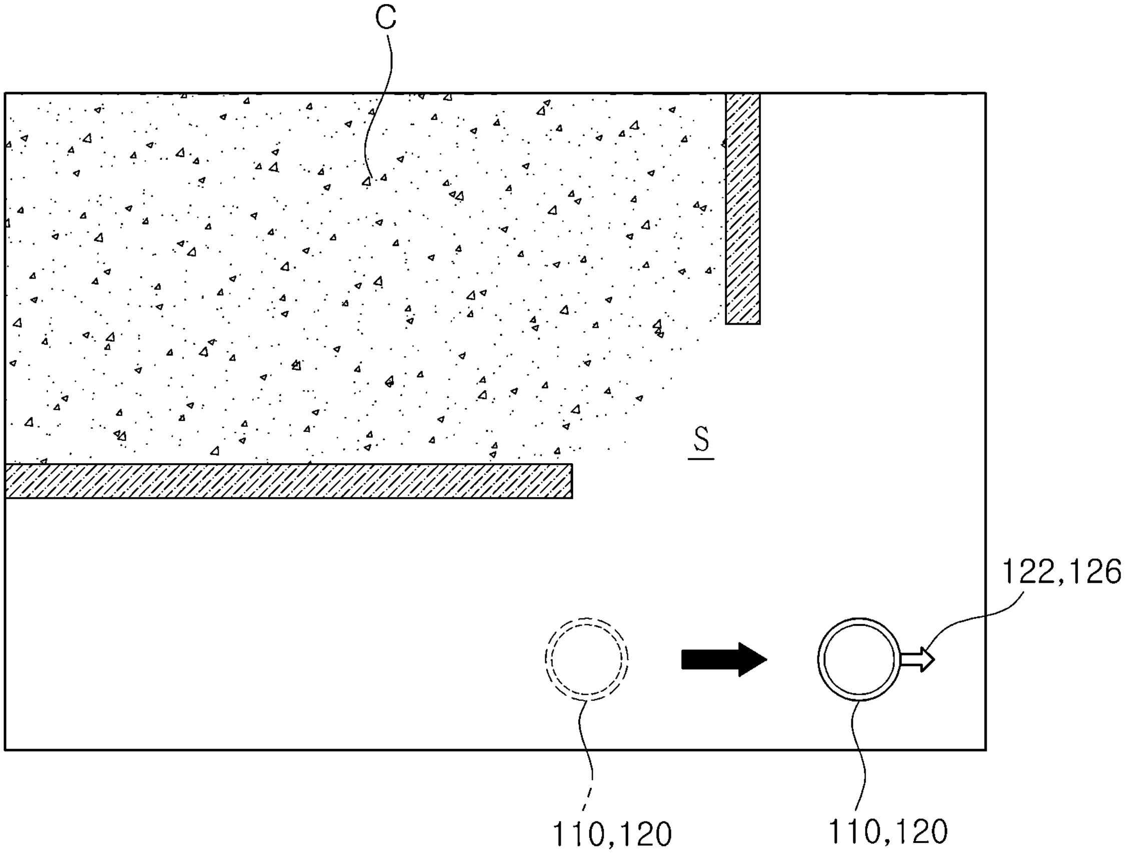
FIG. 16 is a plan view illustrating a state in which the driving unit and the air conditioning module are moving based on information obtained by a detection unit, according to the present embodiment.
Figure 17:
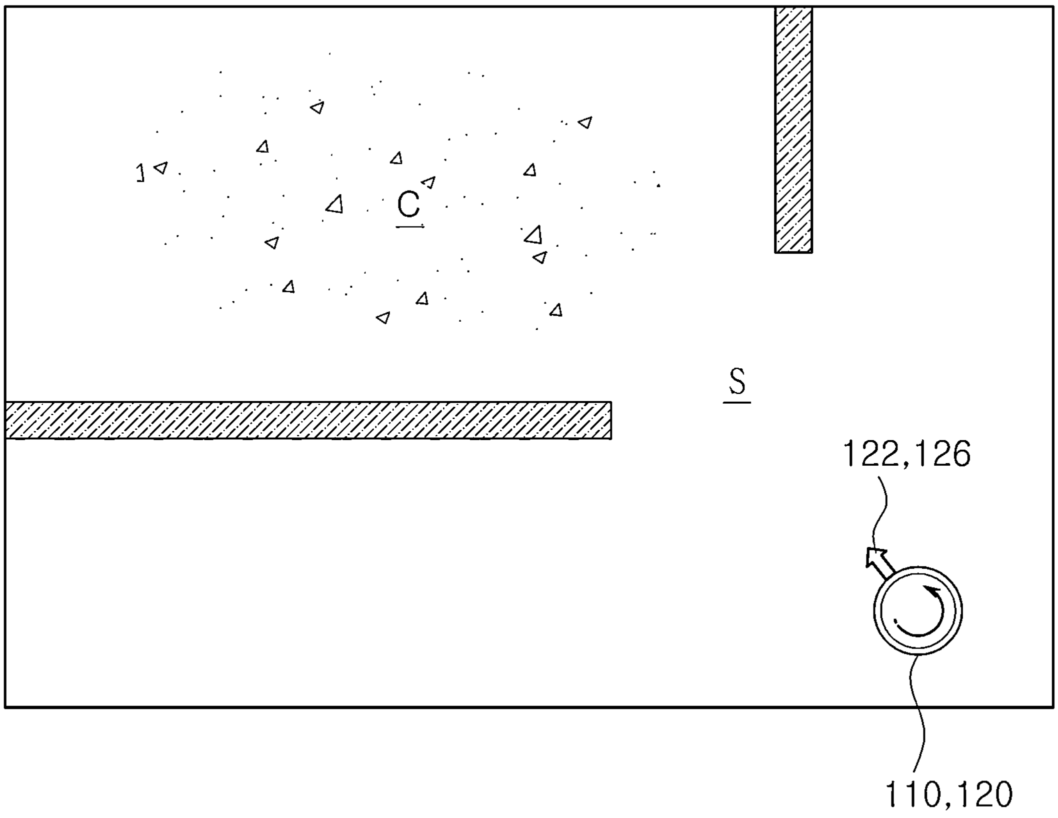
FIG. 17 is a plan view illustrating a state in which the discharge port or the spray port of the air conditioning module is adjusted based on the information obtained by the detection unit, according to the present embodiment.

FIG. 16 is a plan view illustrating a state in which the driving unit 110 and the air conditioning module 120 move based on information obtained by the detection unit 150 according to the present embodiment, and FIG. 17 is a plan view illustrating a state in which the discharge port 122 or the spray port 126 of the air conditioning module 120 is adjusted based on information obtained by the detection unit 150 according to the present embodiment.

Referring to FIG. 16, the controller may obtain map information on a size, a shape, and the presence of obstacles in a target space S according to information detected by the environmental recognition unit of the detection unit 150, and may obtain air quality information according to information detected by the pollution detection unit. The controller operates the driving unit 110 based on the information obtained by the environmental recognition unit and the pollution detection unit to move the driving unit 110 and the air conditioning module 120 to an optimal position at which the purification or disinfection operation of a harmful substance C can be performed. In an example, when the controller operates one driving unit 110 and air conditioning module 120 to uniformly perform air purification or disinfection operation over a wide range of target space S, the controller operates the driving unit 110 to move the driving unit 110 to a wall or column of the target space S (see FIG. 16).

Then, the controller may rotate and adjust the discharge port 122 or the spray port 126 of the air conditioning module 120 toward a relatively wide area or an area with a large amount of harmful substance C so that the air conditioning module 120 can efficiently and quickly proceed with the air purification or disinfection operation, and the controller may rotate the discharge port 122 or the spray port 126 of the air conditioning module 120 by steering the driving unit 110, or the discharge port 122 or the spray port 126 may be rotated through a motorized device mounted on the air conditioning module 120 itself. Further, when it is desired to perform a comprehensive operation over a wider area, or when it is determined that the driving unit 110 is difficult to access due to obstacles, the controller may elevate the discharge port 122 or the spray port 126 of the air conditioning module 120 to perform the operation.

The present disclosure has been described with reference to the limited embodiments and the drawings, but the present disclosure is not limited thereto. The described embodiments may be changed or modified by those skilled in the art to which the present disclosure pertains within the technical spirit of the present disclosure and within the scope equivalent to the appended claims.

What is claimed is:

1. An air cleaning and disinfection robot comprising:
- a driving unit configured to move autonomously in a target space;
- a plurality of air conditioning modules configured to manage air quality in the target space and detachably provided on the driving unit;
- a station on which the plurality of air conditioning modules are mounted;
- a docking unit configured to couple and separate the driving unit and each of the air conditioning modules to and from each other; and
- a detection unit configured to detect an operation environment of the target space, wherein the driving unit selectively couples to and moves with any one of the plurality of air conditioning modules based on information obtained by the detection unit, wherein the station includes:
- a main frame forming a body;
- a plurality of mounting spaces formed inside the main frame to receive the plurality of air conditioning modules, respectively;
- a mounting frame configured to support each of the air conditioning modules in each of the mounting spaces; and
- a plurality of detachable spaces each formed at lower sides of the plurality of mounting spaces to allow the driving unit to enter, wherein the docking unit includes:
- a first docking member provided on a lower surface of each of the air conditioning modules and having a protrusion formed to protrude downward;
- a second docking member provided on an upper surface of the driving unit and having a seating portion into which the protrusion is inserted; and
- an elevating and lowering device provided on a side of the driving unit to elevate and lower the second docking member.

2. The air cleaning and disinfection robot of claim 1, wherein the docking unit further includes a detachable portion provided between the protrusion and the seating portion, and
- the detachable portion includes: a plurality of balls formed to protrude along an outer circumference of the protrusion and elastically supported; and
- a groove formed to be recessed along an inner circumference of the seating portion and into which at least a portion of the plurality of balls is inserted.

3. The air cleaning and disinfection robot of claim 2, wherein the protrusion is formed in a cylindrical shape, and
- the seating portion is formed hollow such that the protrusion is inserted thereinto and provided such that the first docking member and the second docking member are rotatable relative to each other.

4. The air cleaning and disinfection robot of claim 2, wherein the first docking member includes a first rotator provided with the protrusion and configured to be rotatable relative to the first docking member, and
- the second docking member includes a second rotator provided with the seating portion and configured to be rotatable relative to the second docking member.

5. The air cleaning and disinfection robot of claim 4, wherein the docking unit further includes:
- at least one fastening pin formed to extend in an upward and downward direction in any one of the first rotator or the second rotator; and
- at least one fastening hole formed to be recessed in the upward and downward direction in the other of the first rotator or the second rotator and in which the fastening pin is inserted.

6. The air cleaning and disinfection robot of claim 4, wherein the first docking member further includes a first opening in which the first rotator is rotatably received, and
- the second docking member further includes a second opening in which the second rotator is rotatably received.

7. The air cleaning and disinfection robot of claim 1, wherein the elevating and lowering device includes a plurality of link members connected to the second docking member, wherein adjacent link members are hinged to each other, and
- a docking drive unit configured to extend or shorten the plurality of link members in an upward or downward direction by rotating or moving at least one of the link members.

8. The air cleaning and disinfection robot of claim 1, wherein the plurality of air conditioning modules include:
- at least one purification device configured to suction, purify, and discharge air of the target space; and at least one disinfection device configured to spray a disinfectant into the target space.

9. The air cleaning and disinfection robot of claim 8, wherein the detection unit includes:

an environmental recognition unit configured to recognize a surrounding environment of the target space by detecting at least one of a size, a shape, or an obstacle of the target space; and a pollution detection unit configured to detect an air pollution level in the target space.

10. The air cleaning and disinfection robot of claim 9, wherein each of the purification devices includes a filter configured to filter out harmful substances, such as dust, included in the suctioned air, and each of the disinfection devices includes a storage tank in which the disinfectant is received.

11. The air cleaning and disinfection robot of claim 10, further comprising a controller configured to control operations of the air conditioning module, the driving unit, and the docking unit based on information obtained by the detection unit.

12. The air cleaning and disinfection robot of claim 11, wherein each of the purification devices includes:

a first main body in which the filter is provided; and a discharge port through which the air purified through the filter is discharged, each of the disinfection devices includes: a second main body in which the storage tank is provided; and a spray port from which the disinfectant is sprayed, the discharge port is provided to be rotatable, or elevated or lowered with respect to the first main body, and the spray port is provided to be rotatable, or elevated or lowered with respect to the second main body.

13. A method of operating the air cleaning and disinfection robot of claim 11, the method comprising operating, by the controller, the driving unit to allow the purification device to enter the unoccupied mounting space when a flow rate of air passing through a filter of any one of the purification devices is less than a preset flow rate, when an operating time of any one of the purification devices exceeds a preset time, or when an operation switch signal of a user occurs.

14. The method of claim 13, wherein the controller configured to:

after operating the driving unit to allow the purification device to enter the unoccupied mounting space, operate the docking unit to mount the purification device on the mounting frame and separate the driving unit from the purification device;

operate the driving unit to access and move to the mounting space in which the other purification device in standby for operation or the disinfection device in standby for operation is mounted; and operate the docking unit to couple the driving unit to the other purification device in standby for operation or the disinfection device in standby for operation.

15. The method of claim 13, wherein the controller operates the docking unit to elevate the purification device from the driving unit before operating the driving unit to allow the purification device to enter the unoccupied mounting space.

16. A method of operating the air cleaning and disinfection robot of claim 11, the method comprising operating, by the controller, the driving unit to allow the disinfection device to enter the unoccupied mounting space when a level of disinfectant received in a storage tank of any one of the disinfection devices is lower than a preset level, when an operating time of any one of the disinfection devices exceeds a preset time, or when an operation switch signal of a user occurs.

17. The method of claim 16, wherein the controller configured to: after operating the driving unit to drive the disinfection device to enter the unoccupied mounting space, operate the docking unit to mount the disinfection device on the mounting frame and separate the driving unit from the disinfection device;

operate the driving unit to access and move to the mounting space in which the other disinfection device in standby for operation or the disinfection device in standby for operation is mounted; and operate the docking unit to couple the driving unit to the other disinfection device in standby for operation or the purification device in standby for operation.

18. The method of claim 16, wherein the controller operates the docking unit to elevate the disinfection device from the driving unit before operating the driving unit to allow the disinfection device to enter the unoccupied mounting space.

* * * * *